United States Patent [19]

Ritchey

[11] 4,146,605

[45] Mar. 27, 1979

[54] ALUMINUM COMPOUNDS AS ANTI-CALCULUS AGENTS

[75] Inventor: Thomas W. Ritchey, Norwood, N.J.

[73] Assignee: Lever Brothers Company, New York, N.Y.

[21] Appl. No.: 840,357

[22] Filed: Oct. 7, 1977

[51] Int. Cl.² ............................................. A61K 7/16
[52] U.S. Cl. ...................................... 424/49; 424/154
[58] Field of Search .................................. 424/48–58, 424/154

[56] References Cited

U.S. PATENT DOCUMENTS

| | | | |
|---|---|---|---|
| 3,175,951 | 3/1965 | Tucker et al. | 424/52 |
| 3,728,446 | 4/1973 | Roberts et al. | 424/49 |
| 3,772,431 | 11/1973 | Mlkvy et al. | 424/49 X |
| 3,888,976 | 6/1975 | Mlkvy et al. | 424/49 X |

FOREIGN PATENT DOCUMENTS 40-14320  8/1965  Japan ......................................... 424/52

*Primary Examiner*—Shep K. Rose
*Attorney, Agent, or Firm*—James J. Farrell; Melvin H. Kurtz; Kenneth F. Dusyn

[57] ABSTRACT

A method and a composition for retarding calculus are disclosed. The composition includes aluminum compounds, which when titrated with NaF have an F/Al ratio of about 1.2 or greater, in combination with an orally acceptable vehicle. The vehicle is compatible with the aluminum compound used and with the pH desired. The method generally includes applying the aluminum compound at a pH of less than about 4.5 to the site of the calculus.

13 Claims, No Drawings

ALUMINUM COMPOUNDS AS ANTI-CALCULUS AGENTS

The present invention relates to a novel method and compositions for controlling calculus.

Dental calculus originates, it is generally believed, with dental plaque which is a layer or deposit that forms on the surface of teeth if one brushes inadequately. Qualitatively, plaque consists primarily of closely matted microorganisms embedded in what is considered to be a partially salivary proteinaceous matrix containing epithelial cells and leucocytes. It is generally accepted that both the bacterial and non-bacterial components of plaque are mineralized to form calculus which includes in addition to mineralized bacteria, organic substituents, such as epithelial cells, live bacteria, salivary proteins, leucocytes, and crystals of substances having molecularly bond calcium and phosphorous, e.g. hydroxyapatite, $3[Ca_3(-PO_4)_2]Ca(OH)_2$, octa-calcium phosphate, $Ca_8(HPO_4)_2(PO_4)_4.5\ H_2O$, brushite, $CaHPO_4.2\ H_2O$ and whitlockite, which is considered to have the formula $beta\text{-}Ca_3(PO_4)_2$. Clinical supra-gingival calculus (tartar) is thus a type of dental plaque which has crystallized with the formation of an hydroxyapatite crystalline structure. The calcium to phosphate ratio for supragingival and sub-gingival calculus commonly varies from 1.28 to 1.55 as compared to a theoretical ratio of 1.66 for hydroxyapatite. Dental calculus is thus seen to be a hard calcified formation on the teeth which is particularly prone to form at the gingival margin, i.e. the junction of the tooth and gingiva. Oral hygiene procedures such as regular toothbrushing usually prevent the rapid build up of calculus deposits, however, in some cases formation of calculus even with regular and thorough brushing is common and in this instance calculus must be removed by a dentist.

Calculus, like plaque, is considered to be a prime causative factor in periodontal disease.

A brief discussion of the pertinent art follows.

Aluminum has been used for many years in connection with dentifrices, both as an abrasive in the form of alumina and as a lining for toothpaste tubes. Generally, the pH of toothpastes on the market ranges from about 4.8 for those containing stannous fluoride to about 10.0. Due to the extremely small solubility product of aluminum hydroxide, only negligble amounts of aluminum are actually in solution at these pH's; and thus in current dentifrices no anticalculus benefits are derived within the scope of the instant invention.

Exemplary of several patents containing alumina in various insoluble forms for oral use are U.S. Pat. Nos. 2,010,910; 2,064,885; 2,981,656; 3,651,207; 3,728,446; 3,726,961; 3,860,705; and 3,928,555. These patents either are directed towards oral use or contain mention that the composition disclosed may be utilized orally. In all of these cases, the aluminum is insoluble as it is basic or in the form of aluminum chlorohydrate. The aluminum compounds used in these patents are largely insoluble and thus the amount of available aluminum would be extremely low and would not provide the anticalculus controlling properties of the instant invention.

U.S. Pat. No. 1,086,193 utilizes aluminum sulfate in combination with boric acid as components in a composition which evolves sodium hydroxide contiguous to tissue for use as an antiseptic. This composition may be used for dental purposes, however, the pH is high enough to prevent the existence in solution of a sufficient amount of aluminum ions to control calculus.

U.S. Pat. No. 2,981,656 contains a gastric acid counteracting composition which is generally an anti-ulcer component. The aluminum compounds used are insoluble and are quite basic.

U.S. Pat. No. 3,728,446 contains aluminum sulfate which in turn when admixed with the composition forms a water-insoluble salt with a gelling agent utilized, such as for example, calcium carboxymethylcellulose. This composition is directed towards a speckled dentifrice gel having an essentially insoluble salt.

U.S. Pat. No. 3,726,961 contains an alkali metal aluminum acid orthophosphate and a reactive trivalent inorganic aluminum compound to form a total crystalline product. The product is taught to be supposedly insoluble in aqueous solutions and thus does not provide sufficient aluminum ions in solution to result in anticalculus control.

U.S. Pat. No. 3,928,555 contains speckled particles for dentifrices. These compositions utilized aluminum dihydroxy allantoinate (ALDA) or aluminum chlorhydroxy allantoinate (ALCA). The speckle is said to be effective in promoting healing of inflamed and bleeding gums or periodontal tissue. Both of these components, the ALDA and the ALCA are insoluble in water and low levels of alcohol. In addition, the compounds were tested for their ability to lower the calcium to phosphate ratio in vitro and failed to reduce artificial calculus.

U.S. Pat. No. 3,651,207, similar to U.S. Pat. No. 3,928,555, contains aluminum dihydroxy allantoinate (ALDA) which is ineffective in reducing calcium to phosphorus ratios.

In addition to the above-mentioned patents, several patents disclose materials such as alum. These patents are U.S. Pat. Nos. 380,700; 1,086,193; 1,466,578; 1,558,160; 1,609,591; and 2,010,910. In these patents the compositions mentioned have pH's which are too high for the alum utilized to produce sufficient soluble aluminum ions to result in calculus control.

More specifically and exemplary of several of the above-mentioned patents containing alum as an astringent is U.S. Pat. No. 2,010,910 which contains an example utilizing alumina, corn starch, boric acid, alum and water. A composition, prepared according to the patent, containing 7.0 grams of Bayer process alumina, 1.50 grams of corn starch, 1.00 grams of boric acid, 0.40 grams of alum and 100 ml of water, has an initial pH of about 6.95 to 7.04. In addition, over a period of time the pH has a tendency to rise. A second of these patents, U.S. Pat. No. 1,466,578 contains honey, borax, alcohol, alum and water. A composition of 21.38 of honey, 3.95 grams of borax, 118 mls of alcohol as described in the patent, 0.71 grams of alum and 946 mls of water has a pH of about 7.11 to 7.17. The pH of both compositions is much too high to release sufficient aluminum ions in solution to result in the benefit of the invention. In the case of the U.S. Pat. No. 1,466,578 patent this omitting only myrtle root has been demonstrated by the lack of any ability to reduce the Ca/P ratio in the Leung dipping test described hereinafter. These two patents are believed to be typical of the type of patent containing alum as an astringent for oral use.

The type of alum used in the above experiments was obtained from both Kirk-Othmer's Encyclopedia of Chemical Technology, 2nd Ed., Vol. 2 p. 63 and the National Formulary, page 51.

In the above formulations the compositions were prepared according to the patent. In each, alum was examined as AlK(SO$_4$)$_2$.12 H$_2$O in a first preparation and as AlNH$_4$(SO$_4$)$_2$.12 H$_2$O in a second preparation. The Bayer process alumina was prepared according to "The Condensed Chemical Dictionary", 5th Edition, 1956 by Reinhold Publishing Company, New York. The pH of each composition was taken seven days after preparation to allow the constituents to equilibrate. Generally then, oral compositions containing alumina or alum do not contain the aluminum ion in such quantity in such state as to be effective against calculus.

U.S. Pat. No. 2,222,969 shows the insolubility of polishing agents, e.g. alumina, and is not directed towards an oral use.

U.S. Pat. No. 2,118,225 is directed to an antiseptic product containing a high concentration of aluminum chloride. The product is not directed towards oral use.

In copending U.S. application, Ser. No. 374,351, zinc compounds have been found to inhibit the formation of calculus. Also, in U.S. Pat. No. 4,022,880 combinations of zinc with certain non-toxic organoleptically acceptable antibacterial agents have been shown to retard the growth of dental plaque in calculus. Zinc, however, does have a certain astringency, which astringency is preferably eliminated from oral products. It would therefore be desirable to find a substitute for zinc.

Accordingly, an object of the present invention is to provide a new method and composition for controlling calculus.

Other objects and advantages will appear as the description proceeds.

The attainment of the above objects is made possible by this invention which includes (1) a composition having a pH of less than about 4.5 for controlling calculus comprising: as an active ingredient, an anticalculus effective amount of an aluminum containing compound or mixture of compounds, said aluminum being substantially in the ionic form, said compound having an F/Al ratio when titrated by NaF greater than about 1.2 in admixture with an acceptable oral medium which is compatible with said composition, and (2) a method for controlling calculus comprising applying to the site of said calculus, an anticalculus effective amount of an aluminum containing compound, said aluminum being substantially in the ionic form, said compound having an F/Al ratio of greater than about 1.2.

The subject invention, encompassing novel compositions and methods for the control of calculus, overcomes one or more of the disadvantages of the prior art heretofore described. This is accomplished with the advantage that the calculus may be controlled with relatively less astringent and relatively safe compounds.

The invention is hereinafter set forth in more detail, specific features thereof being delineated in the appended claims.

Generally, the type of aluminum compound suitable for use in the present invention is an alumumin compound which has an F/Al ratio of 1.2 or greater when titrated with NaF.

Due to the extremely complex chemistry of aluminum, it is difficult to predict the actual concentration of aluminum ion in the solution of an aluminum salt of known concentration. One method for determining aluminum concentration is titration against a fluoride ion. This method was described in a paper by Jaselskis et al entitled "Determination of Micro and Simi-Micro Amounts of Aluminum Using Fluoride Activity Electrode" *Analytical Chemistry*, 41: 855, 1969. The F/Al ratio of aluminum compounds is determined by utilizing 5 mls of a solution containing a 0.0041 moles of aluminum as determined by atomic absorbance. This solution is buffered to pH 3.8 with acetic acid-acetate-sodium perchlorate buffer and titrated with 0.08 molar sodium fluoride.

Due to the extremely slow response time of the fluoride activity electrode at small fluoride concentrations, a blank could not be determined by simply titrating pure buffer with aluminum salt. Instead of a simple determination of the blank, titrations were done of solutions having aluminum concentrations of $2 \times 10^{-5}$M and $4 \times 10^{-5}$M, and the line extrapolation to Al = 0 was taken as the blank. The blank in the instant case took approximately 0.144 milliliters.

The F to Al ratio (F/Al) is taken as an indication of the concentration of active aluminum or aluminum ion in solution. Ideally, this ratio should be 3:1 for aluminum compounds which are completely ionic. However, due to the formation of various aluminum fluoride complexes (e.g. AlF$^{+2}$, AlF$_2{}^+$) the ratio is generally less. The higher the ratio, the more active aluminum is in solution.

Following is a list of compounds with their F/Al ratio determined:

TABLE I

| Compounds | F/Al Ratio |
|---|---|
| H$_2$O | — |
| Al EDTA | 0.41 |
| Al Chlorohydrate | 0.60 |
| Al Citrate | 1.19 |
| Al Lactate | 1.81 |
| Al Phenolsulfonate | 1.90 |
| AlK(SO$_4$)$_2$ | 1.95 |
| Al Cl$_3$ | 2.10 |
| Al$_2$(SO$_4$)$_3$ | 2.19 |

Aluminum lactate, aluminum phenolsulfate, aluminum potassium sulfate, aluminum chloride and aluminum sulfate all have ratios above about 1.2 and thus all of these aluminum compounds are operable with the invention.

The effectiveness of aluminum compounds as anticalculus agents was assayed by means of the Leung dipping technique with certain modifications. The Leung dipping technique is described in detail in the article by S. W. Leung entitled "A New Method for the In Vitro Production of Artificial Calculus", (J. Periodontology, Vol. 28, page 217, 1956). The method was modified for improved quantitation of data, convenience and correspondence of application with the oral use solution.

The principle of the method is to dip glass plummets in and out of saliva or other calculigenic material such as porcine submaxillary gland extracts, allowing time for the saliva to partially dry on the surface of the plummet. After a 3-5 day dipping period, a dental plaque-like deposit is evident and after about 8 or more days of dipping a calculus-like crystalline deposit is found on the surface of the plummet. By treating the plummets daily with the potential anticalculus agents one can physically and chemically compare the type and extent of deposits appearing on the treated plummets with deposits appearing on untreated control plummets. In this manner observations of plaque or calculus formation can be made. The formation of calculus is normally characterized by examining the deposits formed by x-ray crystallography. This examination will show whether the deposits found on the plummet are amorphous or have developed x-ray pattern characteristic of crystalline hydroxyapatite. A chemical analysis of the deposit yields the exact Ca/P ratio. Reductions in the Ca/P ratio reflect reductions in the hardness of the calculus.

In the instant test, the creation of the calculus was simulated on the glass plummets by continuously dipping them in a calcifying solution. Each dipping cycle consisted of a 30 second immersion in the solution followed by 30 seconds of air drying. The dipping apparatus was enclosed in a constant temperature cabinet at 36° plus or minus 1° C. at high humidity. Daily anticalculus treatment consisted of 5 minutes dipping in distilled water, 1 minute immersion in a test solution followed by a 5 minute dipping in distilled water. Dipping in calcifying solution was then repeated.

The calcifying solution was made with porcine glycoprotein which has similar properties to human mucin. The submaxillary gland of a pig was minced, extracted 3 times with water in a Waring Blender for 5 minutes each, stirred at low speed for 18 hours, centifuged in 250 ml bottles at 15,000 gravities for 30 minutes, and lyophlyzed in a Stokes Freeze Dryer for two days. All procedures are carried out at 4° C.

A new calcifying solution was prepared each day by adding the lyophylized mucin to 135 mls of calcium carbonate solution and 15 mls of phosphate buffer, then bubbling with $CO_2$ until the mucin dissolved. The daily mucin concentration was adjusted to obtain an observed uniform calculus deposit. The calcium carbonate solution was prepared every two weeks by adding 0.070 grams of calcium carbonate to 540 mls of water and bubbling with $CO_2$ until the carbonate dissolved. The phosphate buffer (pH 7) was a mixture of 8 grams of sodium dihydrogen phosphate and a 9.47 grams of disodium hydrogen phosphate in a liter of water prepared every 2 months.

After 8 days of dipping, the plummets were dessicated for 24 hours at 40° C. and analyzed for calcium and phosphorus. A reduction of the calcium to phosphorus ratio over the control (pure water instead of an aluminum salt) was taken to mean that there was an inhibition on the formation of calculus. Since the calcium to phosphorus ratio of actual calculus may be as low as 1.28, ratio of less than 1.28 were desired. Using the foregoing Leung screening technique, a variety of aluminum compounds were tested for anticalculus activity. The following results were obtained:

TABLE II

| Compound | F/Al | Ca/P | % error |
|---|---|---|---|
| $H_2O$ | — | 1.46 | 3.4 |
| Al EDTA | .41 | 1.43 | 3.4 |
| Al Chlorohydrate | .60 | 1.42 | 4.9 |
| Al Citrate | 1.19 | 1.35 | 9.1 |
| Al Lactate | 1.81 | 1.19 | 6.7 |
| Al Phenolsulfonate | 1.90 | 1.22 | 3.2 |
| Al $K(SO_4)_2$ | 1.95 | 1.19 | 4.2 |
| Al $Cl_3$ | 2.10 | 1.18 | 6.7 |
| $Al_2(SO_4)_3$ | 2.19 | 1.19 | 6.7 |

The minimum amount of the aluminum compound or mixture of compounds necessary to result in a control of calculus is generally about 0.001 molar at the site of formation. While there is no maximum effective concentration, amounts significantly higher than about 0.025 molar will be difficult to formulate in an organoleptically acceptable manner. In essence then, the invention consists of the aluminum at a concentration of at least 0.001 molar in a proper vehicle for application to calculus. The maximum concentration, which can be utilized, is thus properly determined by product parameters such as astringency and toxicity. These molar concentrations are expressed as the amount of generally ionic aluminum in solution.

The concentration of aluminum containing compound combined with a vehicle to form the compositions of this invention is not critical and may vary within organoleptically acceptable limits so long as the amount of compound is sufficient to result in a concentration of 0.001 to 0.01 molar at the site of formation of the calculus.

In order for the aluminum compound to be effective as an anticalculus agent, the pH of the composition or the pH of the environment in which the aluminum is applied must be suitably low. This is necessary to insure that the proper amount of aluminum will be available to act as an anticalculus agent.

While not wishing to be bound by the following theory, it is thought that the volume of the oral product and the buffering capacity of that product at pH 4.0 exceeds the buffering capacity of the saliva so that upon introduction the aluminum has sufficient time to reach the site of the calculus.

The pH of the composition may be generally about 4.5 or less, preferably about 3.8 to about 4.4, to increase the solubility of the aluminum compound while minimizing possible irritancy of the vehicle and optimally the pH is about 4.0 to about 4.2. If the pH is too high, flocculation may result which forms insoluble aluminum hydroxide and gives a reduction in anticalculus activity. To verify the pH dependence of the aluminum compound, it is possible to calculate the expected maximum concentration of aluminum at a given pH from the solubility product of aluminum hydroxide $[Al][OH]^3 = 2 \times 10^{-32}$. The following table compares pH with maximum aluminum ion concentrations.

TABLE III

| pH | [Al] |
|---|---|
| 6.2 | $5.08 \times 10^{-9}$ |
| 4.8 | $7.89 \times 10^{-5}$ |
| 4.65 | $2.24 \times 10^{-4}$ |
| 4.23 | $4 \times 10^{-3}$ |
| 4.17 | $6 \times 10^{-3}$ |
| 4.10 | $1 \times 10^{-2}$ |
| 4.0 | $2 \times 10^{-2}$ |
| 3.8 | $7.89 \times 10^{-2}$ |
| 3.5 | $6.32 \times 10^{-1}$ |
| 3.0 | $2 \times 10^{+1}$ |

From a study of this Table it is clear that there is not enough aluminum in solution until a pH of about 4.4 to 4.5 is reached for marginal anticalculus activity. Not until the pH equals 4.0–4.2 is there an opportunity to achieve a substantial anticalculus effect without using excessive amounts of aluminum. Additional proof will be offered in Example II. In view of this, the aluminum is preferably applied from a composition having a pH of 4.1 or less.

Generally, there are three critical parameters relating to the use of aluminum salts or aluminum compounds as anticalculus agents within the ambit of the instant invention.

1. Type of aluminum containing compound: The compound must be substantially ionic in character. When titrated with sodium fluoride, the F/Al ratio, after correction for the blank, must be greater than about 1.2.
2. Concentration: The minimum effective amount of the aluminum concentration is about 0.001. While there is no maximum effective concentration, the maximum concentration employed is properly determined by product considerations, such as astringency and toxicity.

3. pH: The pH of any product of the invention has to be below about 4.5 in order to achieve an effective aluminum concentration. Minimum pH is, of course, like maximum concentration, a function of product considerations.

Once the three critical parameters have been met, the aluminum compound of the instant invention may be utilized with a variety of orally compatible agents, such as mouthwashes, toothpastes, dentifrices, tooth powders, lozengers, chewing gum, as well as any compatible vehicle for applying the aluminum compound to the specific site of calculus formation. Such formulations being generally prepared in accordance with the art recognized practice.

In mouthwash formulations, e.g. the carrier is typically an essentially aqueous solution of alcohol, glycerine or sorbitol. In some mouthwash formulations it is not essential to use any of these materials, although it does help to solubilize certain flavor oils and it can make the product smoother and impart body to it. Additionally, several of these components are useful as an aid in sweetening the product. Surfactants or suspending agents are also present in mouthwash as solubilizers for essential flavor oils. The customary solubilizers for this purpose are polyoxyethylene sorbitan fatty acid esters, sorbitan fatty acid esters and polyoxyethylene fatty acid esters.

In toothpaste and tooth powder formulations, the essential ingredient other than the aluminum compound of this invention is a suitable dental abrasive. This abrasive must not interact with the aluminum compound. It is recommended that the abrasives used in the dentifrice formulation of the present invention provide a final composition which has a minimum dentin abrasion value of about 50. Suitable dental abrasive substances include magnesium trisilicate, finely divided silicas, a silica embedded in protective plastic particles, bentonite and plastic particles of appropriate size, hardness and composition for dentifrice abrasives.

Toothpaste and tooth powder formulations also commonly contain a soap or synthetic surface active agent. It is essential in these formulations as well as mouthwash formulations to provide sufficient foaming action to satisfy a market consumer preference for this property. A preferred material for dentifrices is sodium lauryl sulfate. However, many other surface active agents can be used so long as they are compatible, i.e. they do not interfere with the activity of the aluminum compound.

In addition, the toothpaste formulation will frequently contain humectants sufficient to provide smooth texture and flowability. Glycerine and sorbitol are preferred for this purpose together with suitable amounts of water, ethyl alcohol, mineral oil, glucose, mannitol, propylene glycol, polyethylene glycols, and other glycols which may also be employed.

Lastly, the toothpaste formulation generally contains selected binding agents. These also should be compatible with the aluminum compound as well as with the other toothpaste components. For example, cellulose ethers are one type of preferred binder. Silica aerosols, precipitated silicas, and pyrogenic or fumed silicas may also be used as a binder for the compositions of this invention.

A chewing gum medium normally comprises a gum base and common flavoring materials used in the field. The flavoring materials are present at a level of about 0.01–2.0% of the final chewing gum composition. The base is a chewable plastic gum material such as natural rubber, chickle, polyvinyl acetate, ester gum, coumarone resin, and paraffin wax. The gum base is typically made from a mixture of two or more plastic gum materials to achieve a preferred degree of plasticity for chewing. Optionally, a binder or a softener may be used as well as sweetening agents. Lozengers may be made containing the aluminum compound, a material to insure that the pH of the compound is at about 4.5 or less and a suitable binder.

It is believed that the active constituent related to anti-calculus activity is the aluminum ion. Possibly, a theory explaining the action of aluminum in the present invention is that aluminum may be involved in an exchange type of reaction taken place at the surface of calculus.

Electron Spectroscopy for Chemical Analysis (ESCA) analysis have been performed on tooth samples which had artificial calculus induced on their surface. The results of these analyses are substantially as follows:

TABLE IV

| Sample No. | Relative Number of Atoms Present at Surface | | | | |
|---|---|---|---|---|---|
| | Ca | P | Ca/P | Al | Zn |
| 1. Control | 8.6 | 6.3 | 1.37 | — | — |
| 2. Control | 12.5 | 10.0 | 1.25 | — | — |
| 3. 0.2% $ZnCl_2$(3x) | 15.5 | 14.3 | 1.09 | — | 2.4 |
| 4. 0.2% $ZnCl_2$(4x) | 18.2 | 16.7 | 1.09 | — | 3.2 |
| 5. 0.36% $AlCl_3$(3x) | 8.0 | 9.3 | 0.86 | 4.5 | — |
| 6. 0.36% $AlCl_3$(4x) | 5.3 | 13.7 | 0.38 | 11.1 | — |

The Ca/P ratio of the control teeth numbers 1 and 2 was similar to scrapings of clinical samples of dental calculus. Rinsing three or four times with 0.2% $ZnCl_2$ lowered the Ca/P ratio and reduced calculus as described in U.S. Pat. No. 4,022,880. Zinc replaced a portion of the calcium in the calculus which resulted in a weaker calcification. Aluminum theoretically inhibited calculus in the same manner.

The following Examples will more fully illustrate the embodiments of this invention. All parts and proportions referred to herein and in the appended claims are by weight unless otherwise indicated.

EXAMPLE I

In an experiment conducted using the Leung dipping test described previously the concentration of aluminum citrate, as reported in Table I, is varied from 0.00083 molar to 0.0117 molar and the calcium to phosphorus ratios noted. While there is a slight improvement at the higher concentrations, aluminum citrate is not really useful as an anticalculus agent. It is suspected that the substantially covalent salts, like the citrate, do not supply enough active aluminum, even at these concentrations, to be used as anticalculus agents. Based on Table I, it appears that the aluminum salt has to give an F/Al ratio in excess of at least 1.2 before it can be used as an anticalculus agent. Such salts are substantially ionic in character.

EXAMPLE II

A. A study is carried out by the Leung dipping test to determine the anticalculus effect of aluminum chloride with respect to concentration and with respect to a clinically tesed zinc chloride. The results of this study are in Table V following:

TABLE V

| Compound | Conc. (M) | pH | Ca/P | Standard Deviation |
|---|---|---|---|---|
| $H_2O$ | — | 7 | 1.50 | .05 |
| $ZnCl_2$ | .014 | 4.30 | .97 | .04 |
| $AlCl_3$ | .0019 | 4.05 | 1.37 | .03 |
| $AlCl_3$ | .0037 | 4.00 | 1.33 | .04 |
| $AlCl_3$ | .0074 | 3.90 | 1.14 | .03 |
| $AlCl_3$ | .0074* | 4.65 | 1.29 | .09 |
| $AlCl_3$ | .015 | 3.70 | .87 | .09 |
| $AlCl_3$ | .025 | 3.60 | .64 | .05 |
| $AlCl_3$ | .025* | 4.00 | .65 | .06 |

*pH adjusted with NaOH.

It can be seen that substantial calculus reduction occurs at about the 0.0074 molar level which gives a Ca/P ratio of 1.14. If a dose response graph is constructed from the Ca/P ratios then 0.001 molar aluminum exhibits statistically significant reductions in the Ca/P ratio (calculus). Based on correlation with clinical studies, clinical reduction is expected at about 0.01 molar. The optimum level of $ZnCl_2$ was previously determined to be about 0.014 molar, as reported by Schmid et al in an article entitled "Effect of a Zinc Chloride Mouthrinse on Calculus Deposits Formed on Foil", Helv. Odont. Acta, 18 pp. 22–24, April 1974. At this level, aluminum chloride compares well with zinc chloride.

B. A second study is run by the Leung dipping test comparing a rinse prepared according to U.S. Pat. No. 1,466,578, but omitting myrtle root, with 0.2% by weight $ZnCl_2$, water 0.36% by weight, $AlCl_3 \cdot 6H_2O$ and 0.161% by weight EHDP (trisodium ethane-1-hydroxy-1,1-diphosphonate). The results are as follows:

TABLE VI

| Compound | Concentration M | Average Ca/P ratio |
|---|---|---|
| $H_2O$ | — | 1.29 |
| 1,466,578 | — | 1.27 |
| $ZnCl_2$ | 0.015 | 0.98 |
| $AlCl_3 \cdot 6H_2O$ | 0.015 | 0.73 |
| EHDP | 0.015 | 1.04 |

These results show that the aluminum compound tested is statistically better at reducing the Ca/P ratio than equimolar concentrations of $ZnCl_2$ and EHDP, both of which have been shown in vivo to reduce dental calculus.

EXAMPLE III

The following formulations may be utilized to incorporate the aluminum compounds of this invention. The specific aluminum salts used in the formulation are typical of the aluminum salts of this invention.

A. Mouthwash

| | |
|---|---|
| Ethanol | 22.00 |
| Glycerol | 12.00 |
| Flavor, color | .90 |
| Hydrochloric acid (to pH 4.1) | — |
| Aluminum sulfate | .25 |
| Sodium lauryl sulfate | .10 |
| Polyoyethylene 20 Sorbitan monolaurate* | .20 |
| Water Balance to 100% | |

*marketed by Hodag Chemical Copany as Polysorbate 20.

B. Tooth Powder

| | |
|---|---|
| Abrasive | 94.9 |
| Sodium lauryl sulfate | 3.0 |
| Hydrochloric acid (to pH 3.8) | — |
| $Al_2(SO_4)_3$ | .3 |
| Flavor | 1.4 |
| | 100.0% |

C. Toothpaste

| | |
|---|---|
| Particulate polishing agents | 10.00 |
| Humectant (sorbitol) | 40.00 |
| Sodium lauryl sulfate (21%) glycerine | 7.00 |
| Bodying agent (carboxymethylcellulose) | 1.00 |
| Flavor, color | 1.5 |
| Aluminum chloride | .40 |
| Hydrochloric acid (to pH 4.0) | — |
| Water Balance to 100% | |

D. Toothpaste

| | |
|---|---|
| Abrasive | 13.00 |
| Binder | .30 |
| Sorbitol (70% solution) | 64.20 |
| Cab-O-Sil bodying agent | 8.50 |
| Polyethylene glycol, mw 6000 | 1.00 |
| Stannous Fluoride | — |
| Aluminum sulfate | .25 |
| Sodium lauryl sulfate/glycerine | 7.00 |
| Hydrochloric acid (to pH 4.1) | — |
| Flavor, color | 3.00 |
| Water Balance to 100% | |

E. Mouthwash

| | |
|---|---|
| $AlCl_3 \cdot 6H_2O$ | 0.36 |
| Flavor | 0.15 |
| Humectant | 8.00 |
| Saccharin | 0.02 |
| FD&C Yellow No. 6 (0.7% solution) | 0.10 |
| FD&C Red No. 2 (0.2% solution) | 0.12 |
| Sodium lauryl sulfate | 0.33 |
| Hydrochloric acid (to pH 4.4) | — |
| Tween 20 | 0.30 |
| Water Balance to 100% | |

F. Toothpaste

| | |
|---|---|
| Abrasive | 10.00 |
| Aluminum Lactate | 4.5 |
| Refined extract of carragheenan | 0.35 |
| Titanium dioxide | 0.5 |
| Bodying agent (Cab-O-Sil) | 9.00 |
| Saccharin | 0.20 |
| Glycerin (95%) | 60.00 |
| Polyethylene glycol, mw = 400 | 4.00 |
| Hydrochoric acid (to pH 4.2) | — |
| 21% sodium lauryl sulfate in glycerine | 7.00 |
| Coloring and flavor | 1.32 |
| Water Balance to 100% | |

G. Toothpaste

| | |
|---|---|
| Abrasive | 15.00 |
| Powdered polyethylene[1] | 5.00 |
| Carboxymethylcellulose | 0.80 |
| Glycerin | 65.00 |
| Saccharin | 0.20 |
| Aluminum Lactate | 10.25 |
| Flavor | 1.30 |
| Coloring | 0.25 |
| Foaming agent | 0.63 |
| Hydrochloric acid (to pH 4.3) | — |
| Water Balance to 100% | |

[1]The polyethylene is a high density polyethylene powder having an average particle size of about 8-9 microns.

H. Toothpaste

| | |
|---|---|
| Abrasive | 17.00 |
| Polyethylene powder[1] | 5.00 |
| Carboxymethylcellulose | 0.80 |
| Aluminum Chloride | 3.00 |
| Saccharin | 0.35 |
| Glycerin | 55.00 |
| Flavor | 1.30 |
| Foaming agent (sodium lauryl sulfate) | 1.47 |
| Color | 0.25 |
| Acetic acid (pH to 4.2) | — |
| Water Balance to 100% | |

[1]The polyethylene is a high density polyethylene powder having an averge particle size of about 8-9 microns.

The invention has been described with respect to certain preferred embodiments and various modifications and variations in the light thereof will be suggested to persons skilled in the art and are to be included with the spirit and purview of this application and the scope of the appended claims.

What is claimed is:

1. A composition having a pH of about 4.5 or less for controlling calculus: comprising as an active ingredient an anticalculus effective amount of at least one aluminum containing compound, said aluminum being substantially in the ionic form, said compound having an F/Al ratio when titrated by NaF of greater than about 1.2 in admixture with an acceptable oral medium compatible with said composition.

2. A composition as defined in claim 1 wherein said anticalculus effective amount is at least about 0.001 molar.

3. A composition as defined in claim 1 wherein said pH is about 3.8 to about 4.3.

4. A composition as defined in claim 1 wherein said pH is about 4.0 to about 4.2.

5. A composition as defined in claim 1 wherein said aluminum compound is selected from the group consisting of aluminum lactate, aluminum phenolsulfonate, aluminum potassium sulfate, aluminum chloride, aluminum sulfate, and mixtures thereof.

6. A composition as defined in claim 1 wherein said F/Al ratio is about 1.2 to about 2.5.

7. A composition as defined in claim 1 wherein said F/Al ratio is about 1.5 to about 2.3.

8. A composition as defined in claim 1 said acceptable oral medium comprising water.

9. A method for controlling calculus comprising applying to the site of said calculus an anticalculus effective amount of an aluminum containing compound, said aluminum being substantially in the ionic form, said compound having an F/Al ratio of greater than about 1.2 and a pH of about 4.5 or less.

10. A method as defined in claim 9 wherein said anticalculus effective amount is at least about 0.001 molar.

11. A method as defined in claim 9 wherein said aluminum compound is selected from the group consisting of aluminum lactate, aluminum phenolsulfonate, aluminum potassium sulfate, aluminum chloride, aluminum sulfate, and mixtures thereof.

12. A method as defined in claim 9 wherein said F/Al ratio is about 1.2 to about 2.5.

13. A method as defined in claim 9 wherein said F/Al ratio is about 1.5 to about 2.3.

* * * * *